United States Patent
Kwon et al.

(10) Patent No.: US 11,795,447 B2
(45) Date of Patent: Oct. 24, 2023

(54) METHOD FOR EXTRACTING HIGH-PURITY POLYDEOXYRIBONUCLEOTIDE FROM SALMON TESTES

(71) Applicant: Bio Medi pharm Co. Ltd., Gangwon-do (KR)

(72) Inventors: O Nam Kwon, Gangneung-si (KR); Tae-hyun Kim, Yeoju-si (KR); Sun-hee Kim, Seoul (KR)

(73) Assignee: BIO MEDI PHARM CO. LTD., Gangwon-Do (KR)

( * ) Notice: Subject to any disclaimer, the term of this patent is extended or adjusted under 35 U.S.C. 154(b) by 140 days.

(21) Appl. No.: 17/400,612

(22) Filed: Aug. 12, 2021

(65) Prior Publication Data

US 2022/0073553 A1 Mar. 10, 2022

(30) Foreign Application Priority Data

Sep. 7, 2020 (KR) .................. 10-2020-0113706

(51) Int. Cl.
*C12N 15/10* (2006.01)
(52) U.S. Cl.
CPC ................ *C12N 15/1003* (2013.01)
(58) Field of Classification Search
None
See application file for complete search history.

(56) References Cited

FOREIGN PATENT DOCUMENTS

| CN | 107287186 | 10/2017 |
|----|-----------|---------|
| EP | 266 254 | 12/1993 |
| KR | 10-2019-0139633 | 12/2019 |

OTHER PUBLICATIONS

Patrice Rosengrave et al.; "Chemical composition of seminal and ovarian fluids of Chinook salmon (*Oncorhynchus tshawytscha*) and their effects on sperm motility traits"; Comparative Biochemistry and Physiology, Part A; Molecular & Integrative Physiology, Oct. 2008.
Michael J. Bartlett et al.; "Sperm competition risk drives rapid ejaculate adjustments mediated by seminal fluid" eLife Research article, Genomics and Evolutionary Biology; elifesciences.org.; 2017, pp. 1-24.

*Primary Examiner* — Suzanne M Noakes
(74) *Attorney, Agent, or Firm* — KILE PARK REED & HOUTTEMAN PLLC

(57) ABSTRACT

Disclosed is a method for extracting high-purity polydeoxyribonucleotide (PDRN) from salmon testes, including 1) separating semen and immature testicular regions from the testes of a salmonid fish, 2) gently grinding the immature testicular regions, followed by dilution with an artificial seminal plasma, 3) treating the dilution with a predetermined concentration of human chorionic gonadotropin (hCG) to induce artificial sexual maturation of the testicular cells to sperm, 4) centrifuging the testicular dilution after the passage of a predetermined time from the hCG treatment and collecting potentially motile sperm, and 5) extracting PDRN from the collected sperm. The method enables the production of raw materials for PDRN with a 100- to 200-fold higher purity from 20 mL (a maximum of 50 mL) of sperm (semen) collected at one time from a salmonid fish. In addition, the method enables the extraction of PDNR in high yield in a cost-effective and economically viable manner.

6 Claims, 2 Drawing Sheets

METHOD FOR EXTRACTING HIGH-PURITY POLYDEOXYRIBONUCLEOTIDE FROM SALMON TESTES

BACKGROUND OF THE INVENTION

1. Field of the Invention

The present invention relates to a method for extracting high-purity polydeoxyribonucleotide (PDRN) from salmon testes, and more specifically to a method for extracting high-purity PDRN by hormonal treatment of immature testes, which are currently used in other applications.

2. Description of the Related Art

Polydeoxyribonucleotide (PDRN) is present in active substances for tissue regeneration (anagenesis) in living organisms. PDRN is a mixture of chained deoxyribonucleotide polymers consisting of 50 to 2000 base pairs. PDRN is a cell growth activator that has special effects on the regeneration of tissues in the human body, such as ligaments, tendons, and skin, and the alleviation of inflammation.

Only a very small amount of PDRN is present in the human placenta. PDRN involves ethical issues and suffers from difficulty in pharmaceutical productivity. For these reasons, PDRN in fish has been proposed as an alternative to human PDRN. Nucleic acids are abundant in the semen and testes of trout and salmon, but more important is their qualitative superiority. DNA consists of nucleotides, each of which includes a pentose sugar, a phosphate group, and a nitrogenous base such as adenine, guanine, thymine or cytosine. The balance of this combination in trout and salmon is 96.5% identical to that in humans. This similarity is of great significance in that all nucleic acids can be used without being discarded.

PDRN was approved for use in wound treatment and beauty in European countries and other countries. PDRN is prepared mainly by collecting semen from salmon or trout, isolating DNA from the semen, and fragmenting the DNA. The DNA isolation for PDRN preparation has been technically developed and applied to mammals and other species. For example, phenol and chloroform are used to isolate DNA from fish tissues.

Polydeoxyribonucleotide (PDRN) as a DNA fragment is prepared from sperm-containing semen of salmonid fish and is used as a material for therapeutics and cosmetics with excellent pharmacological activities.

PDRN as a high-purity DNA fragment is used for pharmacological purposes. In this case, sperm fluid (or seminal fluid) is centrifuged, washed with a buffer, and extracted with a mixture of ethanol or sodium acetate and isopropanol to obtain PDRN. This extraction process is the basic principle that is used in many patents and by manufacturers.

Semen from the testicles contains large numbers of spermatids, spermatocytes, and spermatogonia, all of which are differentiated into sperm during gametogenesis. Particularly, semen contains a larger number of nurse cells than these germ cells. The nurse cells serve to supply nutrients to the germ cells.

As shown in FIG. 1, the testes of a fish mature while being attached to the dorsal wall of the coelom. The growth of germ cells during sexual maturity leads to an increase in gonadal-somatic index (GSI). The GSI increases to 20 to 50% for female fish and 1 to 5% for male fish. That is, the number of the testes obtained from male fish is not significant.

On the other hand, PDRN extraction necessarily involves centrifugation of semen, enrichment of sperm (or spermatozoa), and isolation of the sperm with an organic solvent. The sperm consists of DNA (i.e. PDRN) as a genome, mitochondria containing ATP that causes the tail to move, and an acrosome that allows the sperm to penetrate the oolemma. PDRN is a target substance of the present invention.

The amount of PDRN in extraction products from semen with an organic solvent is fundamentally different from that from testes. PDRN can be obtained in higher purity from semen. In contrast, when PDRN is extracted from testes containing nurse cells with an organic solvent, various substances soluble in the organic solvent are inevitably extracted.

In CN107287186A ("Patent Document 1"), PDRN is obtained from seminal fluid, which is expressed as semen. KR 1020190139633A ("Patent Document 2"), which was finally rejected in Korea, describes that testes are lyophilized and extracted with an organic solvent to obtain PDRN. The Korean patent publication recognizes that the purity of PDRN obtained from semen is different from that of PDRN obtained from testes and reveals that high-purity PDRN can be extracted with the highest efficiency from sperm (semen).

Therefore, washing and organic solvent extraction have been established as basic techniques for PDRN extraction. Thus, many recent patents have been issued and papers have been published regarding the use of PDRN based on its pharmacological activity or cosmetic effects rather than regarding methods for PDRN extraction.

Once sperm are produced in the testes of salmonid fish, semen is collected. Thereafter, the abdomens are cut open, immature testes are collected, followed by subsequent processing such as lyophilization. The present inventors have surprisingly discovered that dilution of the testes of salmonid fish with seminal plasma depending on the degree of maturity of the testes and subsequent treatment with a hormone such as human chorionic gonadotropin (hCG) lead to the production of a much larger amount of sperm (or semen). For example, a 100- to 200-fold larger amount of semen may be obtained from one salmonid species.

The composition of the seminal plasma (NaCl, 40 mM KCl, 1 mM $CaCl_2$, 20 mM Tris-HCl) is determined based on information on the mineral concentration of semen described in "Rosengrave P, Taylor H, Montgomerie R, Metcalf V, McBride K and Gemmell N J, 2008. Chemical composition of seminal and ovarian fluids of chinook salmon (*Oncorhynchus tshawytscha*) and their effects on sperm motility traits. CBP A 152, 123-129" and information on the artificial seminal fluid described in "Bartlett M J, Steeves T E, Gemmell N J and Rosengrave P C, 2017. Sperm competition risk drives rapid ejaculate adjustments mediated by seminal fluid. eLIFE 6:e28811".

The seminal fluid as a raw material for PDRN mentioned in Patent Document 1 is semen of salmonid fish, not an extract from testes.

EP 0226254B1 ("Patent Document 3") established a process for extracting PDRN from the placenta. However, this patent only mentions that the process is also applicable to other tissues of other animals and fails to introduce any case. In contrast, the present invention proposes a method for extracting PDRN from salmon testes, starting from collection of testes from live or fresh salmon and washing of the testes to remove blood, and is fundamentally different from a method for preparing PDRN from motile sperm produced in the testes despite the use of the same PDRN sources (i.e. testes) in both methods.

The present inventors have made an effort to extract PDRN from immature testes instead of semen or mature testes that have been widely used in the art, and as a result, found that treatment of immature testes with a suitable hormone, particularly human chorionic gonadotropin (hCG), leads to the production of mature sperm from which high-purity PDRN can be extracted. The present invention has been accomplished based on this finding.

PRIOR ART DOCUMENTS

Patent Documents (Patent Document 1) CN107287186A entitled "Polydeoxyribonucleotide for separate the method for polydeoxyribonucleotide from the seminal fluid of fish, obtaining by methods described and application thereof"
(Patent Document 2) KR1020190139633A entitled "Method for extracting PDRN from semen and testes of fish"
(Patent Document 3) EP0226254B1 entitled "Process for obtaining non informational substantially pure polydesoxyribonucleotides having biologic activities, and respective product".

SUMMARY OF THE INVENTION

It is an object of the present invention to provide a method for artificially producing sperm by treatment of testes with hCG to extract a large amount of PDRN from the sperm.

A method for extracting high-purity polydeoxyribonucleotide (PDRN) from salmon testes according to the present invention includes 1) separating semen and immature testicular regions from the testes of a salmonid fish, 2) gently grinding the immature testicular regions, followed by dilution with an artificial seminal plasma, 3) treating the dilution with a predetermined concentration of human chorionic gonadotropin (hCG) to induce artificial sexual maturation of the testicular cells to sperm, 4) centrifuging the testicular dilution after the passage of a predetermined time from the hCG treatment and collecting potentially motile sperm, and 5) extracting PDRN from the collected sperm.

The present invention will now be described in detail.

In the method of the present invention, the salmonid fish is preferably a fish species belonging to a subfamily selected from the group consisting of Salmoninae, Thymallinae, and Coregoninae and is preferably a river salmon caught in an area extending 10 km upstream from the estuary.

In the method of the present invention, in step 1), the immature testicular regions differ in their degree of maturity and have relatively high degrees of maturity representing a sperm motility of at least 0.7%, and in step 3), the hCG is used in an amount of 25 to 200 IU per gram of testes.

In the method of the present invention, in step 4), the predetermined time is preferably 10 minutes to 1 hour, and the immature testicular regions preferably include spermatogonia or spermatocytes. Preferably, the method of the present invention further includes, before step 5), suspending the sperm and adding fresh water to the suspension to allow the sperm to deplete their ATP, achieving high purity of PDRN.

hCG is an abbreviation for human chorionic gonadotropin and refers to a hormone that is detectable in the urine of pregnant women.

When hCG is injected into carp, crucian carp or goldfish that have been bred at 12° C. or lower throughout the year, fertilized eggs can be obtained at any time. Specifically, injection of hCG in an amount of 500 IU/kg or 500 IU/individual allows the female and male gonads to mature, with the result that fertilized eggs can be naturally obtained 12 to 18 hours after injection (from dawn to morning the next day). Injection of a salmon pituitary extract into female eels leads to sexual maturation of gametes (eggs) while weekly injection of hCG at a concentration of 500 IU/kg enables sperm to mature at 3 months. The mature female eggs and the mature sperm meet to form fertilized eggs.

In one embodiment of the present invention, semen and immature testicular regions having different degrees of maturity are separated from the testes of a salmonid fish, immature testicular regions having high degrees of maturity are collected, the collected immature testicular regions are gently ground and diluted with an artificial seminal plasma, the dilution is treated with a predetermined concentration of hCG, the testicular dilution is centrifuged 10-30 minutes after hCG treatment, and potentially motile sperm are collected and used as raw materials for PDRN.

That is, the present invention is directed to the preparation of high-purity PDRN from motile sperm artificially produced in the testes of a fresh salmonid fish. The degree of maturity of fresh testes varies depending on region, but the closer to the genital pore, the more mature the spermatogonia become. As a result of maturation by hCG, one spermatogonium undergoes meiosis to produce spermatids and sperm cells (up to four), achieving a higher yield than the total wet weight of the testes used and eventually leading to an increase in the yield of PDRN. In the Examples section that follows, hCG treatment increased the dry weight (excluding the precipitate) of sperm cells derived from spermatids by 1.6 times and PDRN with a final purity of at least 82% was extracted in a 2.3 to 3.9 times larger amount from an hCG-treated group than from an untreated group. In addition, high-purity PDRN was obtained in a 40.1-fold higher yield, on average, from semen collected at one time from one male and PDRN was prepared in higher purity when mature sperm were brought into contact with environmental water to deplete their ATP.

Approximately 30-50 mL of semen is obtained from one male salmonid fish but only a limited amount (ca. 10-20 mL) is currently available because a large portion of the semen is used for fertilization in South Korea.

The method of the present invention enables the production of raw materials for PDRN with a 100- to 200-fold higher purity from 20 mL (a maximum of 50 mL) of sperm (semen) naturally produced and collected at one time from a salmonid fish. That is, PDRN prepared from the testes of a salmonid fish by the method of the present invention is more concentrated and purer than that obtained from expensive active semen. According to the method of the present invention, PDNR can be prepared in high yield from the semen and testes of trout or salmon. Furthermore, the method of the present invention enables the extraction of PDNR in a more cost-effective and economically viable manner than conventional methods of other companies.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

The individual steps of the method according to the present invention will be described.

Step 1: Separation of Semen and Immature Testicular Regions

Figure 1:
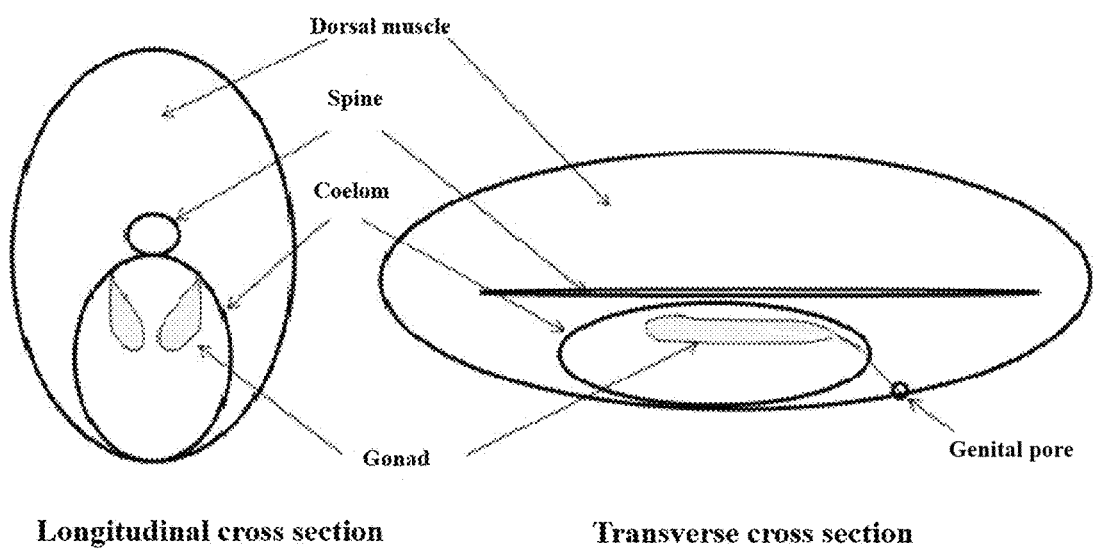
FIG. 1 shows transverse and longitudinal cross-sectional diagrams illustrating the spatial locations of immature gonads (common for both male and female fish) in the coelom of an ordinary fish.
Figure 2:
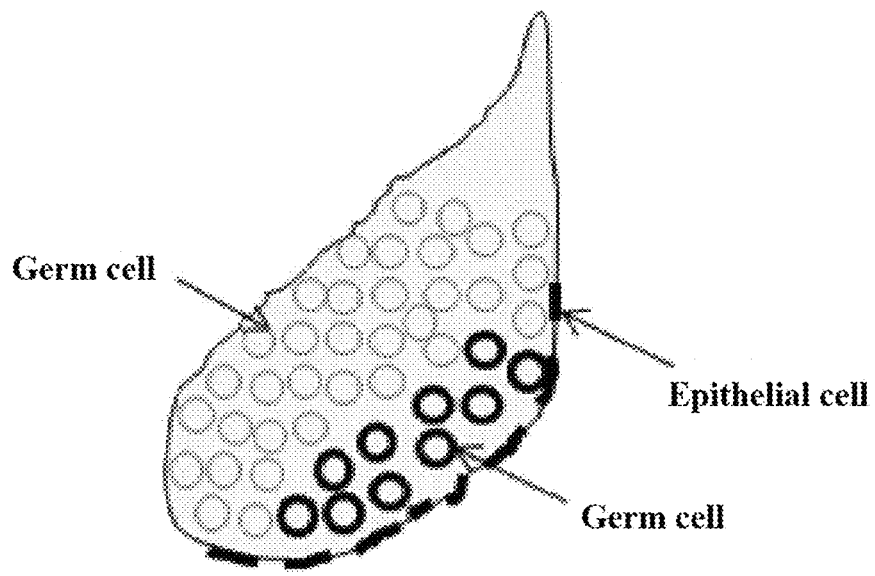
FIG. 2 is an enlarged longitudinal cross-sectional view illustrating an immature gonad (common for both male and female fish) in the coelom of an ordinary fish.
Figure 3:
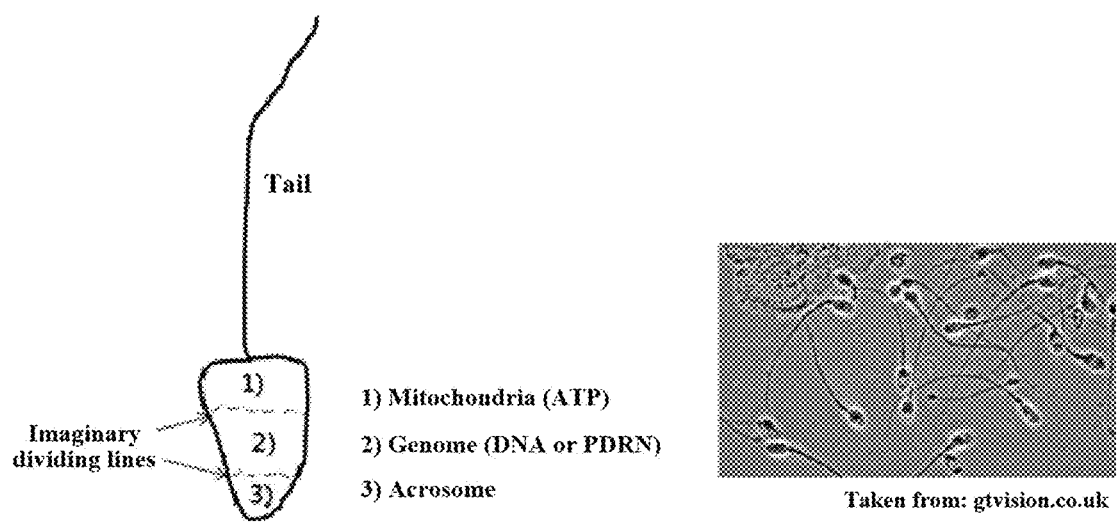
FIG. 3 shows a cross-sectional diagram illustrating the structure of a sperm cell of an ordinary fish (left) and a micrography image illustrating sperm in the semen of an ordinary fish (right)
Figure 4:
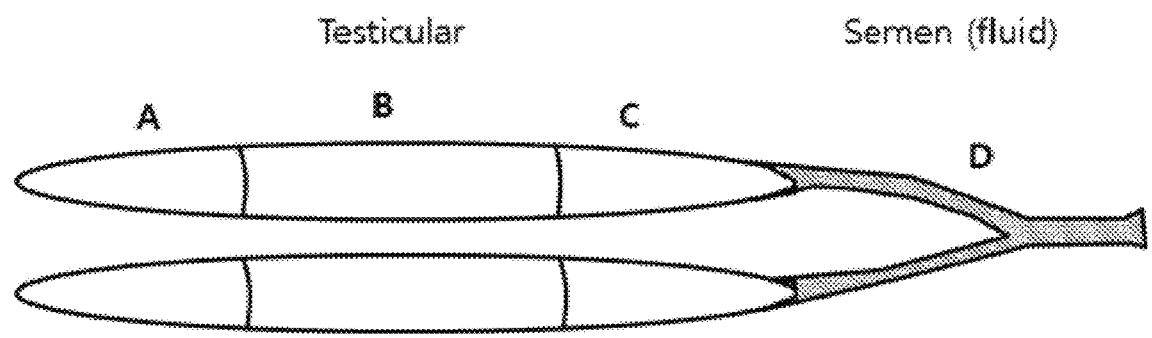
FIG. 4 is a schematic diagram illustrating the locations of different regions of the testis of a mature male salmonid fish.

Semen and immature testicular regions are separated from the testes of a salmonid fish. Semen leaking from region D of FIG. 4 is collected and used as a raw material. After complete withdrawal of the semen from region D, region C is separated from region D by cutting at a predetermined position.

Referring to FIG. 4, the testis is divided into region D where semen leaks out and immature testicular regions A, B, and C. Particularly, most of the sperm from testicular regions A and B are immotile before treatment with hCG and around 1% of the sperm from testicular region C are motile. The sperm in the mature semen from testicular region D have a motility of 100%.

Step 2: Grinding and Dilution of the Immature Testicular Regions

The immature testicular regions A, B, and C are ground and diluted with an artificial seminal plasma. The grinding is performed by the following procedure. First, the testes are cut into small pieces with scissors such that the membranes surrounding the spermatids of the testes are peeled off. Thereafter, the exposed testicular regions A, B, and C are gently crushed with gloved hands.

The seminal plasma has a composition including 80 mM NaCl, 40 mM KCl, 1 mM $CaCl_2$, and 20 mM Tris-HCl, specifically 159.26±8.84 mM sodium (Na), 33.72±2.01 mM potassium (K), 133.04±5.96 mM chlorine (Cl), 1.68±0.2 mM calcium (Ca), and 0.988±0.13 mM magnesium (Mg) (see Hatef A, et. al., 2007. Aquaculture Research 38, 1175-1181). The seminal plasma includes total protein (0.75±0.14 mg 100 $mL^{-1}$), cholesterol (2.86±0.58 mg $L^{-1}$), and glucose (3.81±1.04 mM $L^{-1}$) as organic components.

Step 3: hCG Treatment hCG is an abbreviation for human chorionic gonadotropin. The dilution is treated with hCG at a concentration of 25-200 IU/g to induce artificial sexual maturation of the testicular cells to sperm. Specifically, the dilution is treated with the predetermined amount of hCG under slow stirring with a low-speed impeller agitator. Here, care should be taken because a high speed of the impeller causes cell disruption, increasing the possibility that impurities may increase.

The hCG treatment improves the motility of sperm from testicular regions A to around 3% whereas it increases the motilities of sperm from regions B and C to 35% and 89%, respectively. In conclusion, the use of testicular regions C accounting for 45% of the total weight of the testes for the production of mature sperm would lead to the preparation of high-purity PDRN with few impurities (see FIG. 4 and Table 1).

Step 4: Centrifugation

The testicular dilution is centrifuged at 1,000-10,000 RCF (relative centrifugal force) for at least 20 minutes and potentially motile sperm in the form of precipitates are collected.

Step 5: PDRN Extraction

Polydeoxyribonucleotide (PDRN) is extracted from the collected sperm. Various processes known in the art are applicable to PDRN extraction and a description thereof is thus omitted here. The present invention is characterized by the production of artificial semen from which high-purity PDRN can be extracted, as described above, rather than by the extraction of PDRN.

For example, PDRN may be extracted by the following procedure. First, the sperm are treated with lysis buffer, frozen, and powdered. DNA is isolated by centrifugation and purified by removing proteins. Thereafter, the DNA is precipitated by centrifugation and purified by washing. Finally, the DNA is fragmented by one of the following processes: (1) restriction digest, (2) transmission of high-frequency acoustic energy, (3) nebulization forces, (4) sonication, and (5) needle shearing.

The present invention will be more specifically explained with reference to the following examples. However, these examples are given to provide a thorough understanding of the invention to those skilled in the art, may be changed into several other forms, and are not intended to limit the present invention.

<Example 1> Motilities (%) of Sperm from Different Regions of Salmon Testes Before and after hCG Treatment Immature regions (except for regions D where semen leaks out, see FIG. 4) were collected by cutting the testes of male salmon. The motilities of sperm from testicular regions A and B were almost zero before treatment with hCG. The motility of sperm from testicular regions C was as low as 1% and the motility of sperm in the mature semen was 100%. After hCG treatment, the motility of sperm from testicular regions A was improved to around 3% whereas the motilities of sperm from testicular regions B and C were increased to 35% and 89%, respectively. These results concluded that the use of testicular regions C accounting for 45% of the total weight of the testes for the production of mature sperm would lead to the preparation of high-purity PDRN with few impurities (see FIG. 4 and Table 1).

TABLE 1

Motilities of sperm from different regions of salmon testes before and after treatment with hCG at 100 IU/2 g testis and weight proportions (%) of the testicular regions

| | A | B | C | D |
|---|---|---|---|---|
| Motility before treatment (%) | 0 | 0 | 1 ± 0.3 | 100 ± 0.1 |
| Motility after treatment (%) | 3 ± 5.1 | 35 ± 5.6 | 89 ± 7.2 | — |
| Weight proportion (%) | 15 | 35 | 45 | 5 |

Regions C of the testes of male salmon caught in a river in October were treated with three different types of hormones: hGC, luteinizing hormone-releasing hormone (LhRH), and DHP. When treated with LhRH and DHP, the motilities of sperm were as low as 5 and 4%, respectively. In contrast, the motility of sperm from the experimental group treated with hCG was as high as 80%, making it possible to produce semen with few impurities (Table 2).

TABLE 2

Motilities (%) of sperm from regions C of salmon testes when treated with different types of hormones

|  | hCG | LhRH | DHP |
|---|---|---|---|
| Sperm motility (%) | 80 ± 5.2 | 5 ± 2.8 | 4 ± 3.1 |

The motility of sperm from salmon caught at sea did not increase even after hCG treatment (Table 3). Regions C of the testes of salmon returned to a river between September and December were treated with hCG. As a result, there were no substantial differences in sperm motility because the river salmon were already mature (Table 4). Depending on the distance from an estuary dam, the motilities of sperm were compared. The motilities of sperm from male salmon caught in the estuary dam (distance=0 m) and at a point 1 km upstream from the estuary dam were 65% and 85%, respectively. In contrast, the motilities of sperm from male salmon caught at points 2 km and 3 km upstream from the estuary dam were as high as 97% and 98%, respectively (Table 5).

TABLE 3

Motilities (%) of sperm from regions C of the testes of river salmon (2 km upstream from the estuary) and sea salmon after hCG treatment

|  | River salmon | Sea salmon |
|---|---|---|
| Sperm motility (%) | 80 ± 5.2 | 5 ± 2.8 |

TABLE 4

Motilities (%) of sperm from regions C of the testes of river salmon (2 km upstream from the estuary) caught in different months after hCG treatment

|  | September | October | November | December |
|---|---|---|---|---|
| Sperm motility (%) | 85 ± 11.3 | 97 ± 2.9 | 95 ± 4.8 | 98 ± 3.8 |

TABLE 5

Motilities (%) of sperm from regions C of the testes of river salmon caught at different distances from the estuary after hCG treatment

|  | 0 | 1 km | 2 km | 3 km |
|---|---|---|---|---|
| Sperm motility (%) | 65 ± 8.9 | 85 ± 4.2 | 97 ± 2.7 | 98 ± 1.8 |

The distance from the estuary means the distance from the estuary to a location where salmon went upstream before being caught. hCG hardly acted on the sea salmon, whereas hCG acted on the salmon returning to the river because their sexual maturity had already begun. As can be seen from the results in Table 5, hCG acted better on the salmon caught upstream of the river than on the salmon caught near the sea.

<Example 2> Motilities (%) of Sperm from Regions C of the Salmon Testes Under Different hCG Treatment Conditions Regions C of the testes of male river salmon were diluted with a buffer solution and treated with different concentrations of hCG. The sperm motility was very low (2%) when regions C were untreated, increased steadily with increasing hCG concentration to 50 IU/g, and were ≥82% when treated with hCG at concentrations of 50-200 IU/g (Table 6).

TABLE 6

Motilities (%) of sperm from regions C of the testes of river salmon caught at a point 2 km upstream from the estuary in October when treated with different concentrations of hCG (IU/g testis)

|  | 0 | 25 | 50 | 100 | 200 |
|---|---|---|---|---|---|
| Sperm motility (%)* | 2 ± 2.1 | 30 ± 5.3 | 85 ± 6.1 | 88 ± 3.9 | 82 ± 7.3 |

*Measured 10 min after hCG treatment

The sperm motilities over time after treatment with hCG at the concentrations shown in Table 6 were compared. There were no differences in the motility of sperm from the untreated control even over time. The motility of sperm from the group treated with 25 IU/g testis increased to a maximum of 73% 1 h after treatment and was as high as 85% from 10 min after treatment. The motilities of sperm from the group treated with 50 IU/g testis were as high as ≥94% at 20-30 min after treatment. However, the sperm motility decreased to 83% from 60 min after treatment and sharply decreased to 32% from 60 min after treatment. The motilities of sperm from the groups treated with 100 IU/g testis and 200 IU/g testis began to decrease from 30 min and 20 min after treatment, respectively. That is, the motilities of sperm from the groups treated with 50-200 IU/g testis decreased from when the treatment time exceeded 20 min (Table 7).

TABLE 7

Motilities (%) of sperm from regions C of the testes of river salmon caught at a point 2 km upstream from the estuary in October when treated with different concentrations of hCG(IU/g testis) and over time after treatment

| Conc. (IU/g) | Time (Min.) | | | | |
|---|---|---|---|---|---|
|  | 10 | 20 | 30 | 60 | 120 |
| 0 | 2 ± 2.1 | 2 ± 1.7 | 2 ± 1.9 | 2 ± 0.8 | 2 ± 0.7 |
| 25 | 30 ± 5.3 | 60 ± 8.5 | 70 ± 5.3 | 73 ± 6.7 | 65 ± 12.5 |
| 50 | 85 ± 6.1 | 94 ± 5.3 | 95 ± 7.3 | 83 ± 11 | 32 ± 11.5 |
| 100 | 88 ± 3.9 | 92 ± 6.8 | 91 ± 5.5 | 73 ± 7.6 | 12 ± 5.1 |
| 200 | 82 ± 4.4 | 95 ± 4.9 | 75 ± 7.6 | 52 ± 7.3 | 5 ± 7.3 |

<Example 3> PDRN Extraction Yields (%) when Testicular Regions C were Treated with hCG Under Different Conditions In this example, 10 g of regions C of the testes of male river salmon were used. For comparison, 30 mL of semen normally taken from male river salmon was used (Table 8). The testicular regions were treated with hCG at concentrations of 50 and 100 IU/g testis. After hCG treatment, ≥80% of each top layer was collected and defined as a supernatant.

The dry weight of the untreated group was 5.10 g, which was smaller than those of the hCG-treated groups and was larger than that (2.89 g) of the semen. The larger dry weight of the untreated group than that of the semen was thought to be due to the presence of heavier nurse cells. The larger dry weights of the hCG-treated groups than that of the untreated group was thought to be because the hGC treatment stimulated meiosis of spermatogonia into spermatids, leading to an increase in cell number. The low dry weights of the supernatants after hCG treatment were believed to be because some components (~20%) such as nurse cells remained undifferentiated into spermatids.

Extraction efficiencies of 10.2% and ~14.7% were achieved from the untreated group and the hCG-treated testicular regions, respectively. Extraction efficiencies of 7.0-7.2% and 6.1% were achieved from the supernatants and the semen, respectively. PDRN contents (or purities) of 10% and 45-52% were obtained from the untreated group and 10 g of the testicular regions treated with hCG. In contrast, PDRN purities of ≥92% were achieved from the supernatants and the semen.

Based on these results, the amount of PDRN extracted from one male salmon was calculated. As a consequence, 0.26 g of PDRN was obtained from the semen of one male salmon and 0.16 g of PDRN was obtained from the untreated testicular regions of one male salmon. In contrast, 5.77 and 7.63 g of PDRN were obtained from the testicular regions treated with hCG at concentrations of 50 and 100 IU/g testis, respectively. High-purity PDRN (≥10.51 g) was obtained from the supernatants regardless of the hCG concentration. The yields of PDRN from the untreated group and the testicular regions treated with 50 IU hCG were 0.6-fold and 21.8-fold higher than that of PDRN from the semen, respectively. In contrast, the yields of PDRN from the supernatants after treatment with hCG at concentrations of 50 and 100 IU/g testis were 39.7-fold and 40.1-fold higher than that of PDRN from the semen, respectively.

Since the supernatants were suspensions containing high proportions of sperm, the sperm became motile to deplete ATP in their mitochondria when exposed to environmental water (fresh water). This effect was believed to lead to higher purity of PDRN. Since immotile sperm were precipitated and removed in this course, they needed to be considered in terms of efficiency. However, this consideration did not result in a significant improvement in efficiency due to the high contents (≥92%) of PDRN extracted from the sperm.

TABLE 8

Yields of PDRN from sperm produced in regions C of the testes of river salmon caught at a point 2 km upstream from the estuary in October 20 min after treatment with hCG at concentrations of 0, 50, and 100 IU/g testis

| | | Regions C of the testes of male salmon caught in October (g testis) | | | | | Semen (mL) |
|---|---|---|---|---|---|---|---|
| hCG concentration (IU/g) | | 0 | | 50 IU | | 100 IU | 0 |
| Sample (testis (g) or semen (mL)) | | 10 | | 10 | | 10 | 30 |
| Material used | | All | All | Supernatant[1] | All | Supernatant | All |
| Dilution volume (mL) | | — | — | 100 | — | 100 | — |
| Dry weight (g) | | 5.10 | 6.52 | 5.75[2] | 6.41 | 5.84 | 2.89 |
| Extract weight (g, DM) | | 0.52 | 0.95 | 0.41 | 0.94 | 0.41 | 0.18 |
| Extraction efficiency (%) | | 10.2 | 14.6 | 7.2 | 14.7 | 7.0 | 6.1 |
| PDRN content (%) | | 10 | 45 | 92 | 52 | 93 | 95 |
| Total weight of PDRN (g) | | 0.05 | 0.43 | 0.38 | 0.49 | 0.38 | 0.17 |
| Based on one salmon | Extract weight (g) | 1.56 | 12.83 | 11.43 | 14.66 | 11.41 | 0.28 |
| | Comparison Control | 1.00 | 8.22 | 7.32 | 9.40 | 7.31 | 0.18 |
| | Semen | 5.60 | 46.02 | 41.00 | 52.62 | 40.93 | 1.00 |
| Total weight PDRN from one salmon | | 0.16 | 5.77 | 10.51 | 7.63 | 10.61 | 0.26 |
| Yield (fold) | | 0.6 | 21.8 | 39.7 | 28.8 | 40.1 | 1 |

[1] prepared by sufficiently mixing the testicular regions immediately after hCG treatment, allowing the mixture to stand for 10 min, and collecting ≥ 80% of the top layer.
[2] the higher dry weight after hCG treatment was believed due to meiosis into sperm (chromosome), leading to an increase in cell number.

Although the preferred embodiments of the present invention have been explained in detail, the scope of the present invention is not limited thereto. Those skilled in the art will appreciate that various modifications are possible without departing from the spirit and scope of the invention.

What is claimed is:

1. A method for extracting high-purity polydeoxyribonucleotide (PDRN) from salmon testes, comprising 1) separating semen and immature testicular regions from the testes of a salmonid fish, 2) grinding the immature testicular regions, followed by dilution with an artificial seminal plasma, 3) treating the dilution with human chorionic gonadotropin (hCG) in an amount of 25 to 200 IU per gram of testes to induce artificial sexual maturation of the testicular cells to sperm, 4) centrifuging the testicular dilution 10 minutes to 2 hours after the hCG treatment and collecting potentially motile sperm, and 5) extracting PDRN from the collected sperm, wherein the salmonid fish is a river salmon caught in an area extending 10 km upstream from an estuary.

2. The method according to claim 1, wherein the salmonid fish is a fish species belonging to a subfamily selected from the group consisting of Salmoninae, Thymallinae, and Coregoninae.

3. The method according to claim 1, wherein, in step 1), the immature testicular regions differ in their degree of maturity and have relatively high degrees of maturity representing a sperm motility of at least 0.7%.

4. The method according to claim 1, wherein, in step 4), the time after the hCG treatment is 10 minutes to 1 hour.

5. The method according to claim 1, wherein the immature testicular regions comprise spermatogonia or spermatocytes.

6. The method according to claim 1, further comprising, before step 5), suspending the sperm and adding fresh water to the suspension to allow the sperm to deplete their ATP, achieving high purity of PDRN.

* * * * *